(12) United States Patent
Hu et al.

(10) Patent No.: US 9,222,203 B2
(45) Date of Patent: Dec. 29, 2015

(54) ITEMS OF CLOTHING HAVING SHAPE MEMORY

(75) Inventors: Jinlian Hu, Hong Kong (HK); Jianping Han, Hong Kong (HK); Jing Lu, Hong Kong (HK); Qinghao Meng, Hong Kong (HK); Yong Zhu, Hong Kong (HK); Yan Liu, Hong Kong (HK); Qunmin Ling, Hong Kong (HK); Fenglong Ji, Hong Kong (HK)

(73) Assignee: The Hong Kong Polytechnic University, Hong Kong (HK)

( * ) Notice: Subject to any disclaimer, the term of this patent is extended or adjusted under 35 U.S.C. 154(b) by 591 days.

(21) Appl. No.: 12/827,420

(22) Filed: Jun. 30, 2010

(65) Prior Publication Data

US 2012/0000251 A1 Jan. 5, 2012

(51) Int. Cl.
*D04B 1/24* (2006.01)
*D04B 1/26* (2006.01)
*C08G 18/10* (2006.01)
*C08G 18/42* (2006.01)
*C08G 18/48* (2006.01)
*C08G 18/66* (2006.01)
*D03D 15/00* (2006.01)

(Continued)

(52) U.S. Cl.
CPC ............... *D04B 1/265* (2013.01); *A61F 13/08* (2013.01); *C08G 18/10* (2013.01); *C08G 18/4238* (2013.01); *C08G 18/4854* (2013.01); *C08G 18/664* (2013.01); *C08G 18/6674* (2013.01); *D01F 6/70* (2013.01); *D03D 15/00* (2013.01); *D04B 1/243* (2013.01); *C08G 2280/00* (2013.01); *D10B 2401/046* (2013.01); *D10B 2501/02* (2013.01); *D10B 2501/021* (2013.01)

(58) Field of Classification Search
CPC .......... D04B 1/265; D04B 1/243; D04B 1/24; D10B 2401/046
USPC ................... 57/252; 66/202, 171, 170, 169 R
See application file for complete search history.

(56) References Cited

U.S. PATENT DOCUMENTS 3,616,149 A * 10/1971 Wincklhofer et al. ......... 428/196
3,620,892 A * 11/1971 Wincklhofer et al. ......... 428/197
4,563,384 A * 1/1986 Wiehe et al. ................... 442/153

(Continued)

FOREIGN PATENT DOCUMENTS

GB 1035908 A * 7/1966
GB 1057018 A * 2/1967

(Continued)

OTHER PUBLICATIONS

Tobushi, H., Hara, H., Yamada, E. & Hayashi, S. Thermomechanical properties in a thin film of shape memory polymer of polyurethane series. in Proceeding of the 3rd International Conference on Intelligent Materials, 2779, 418. 1996.

(Continued)

*Primary Examiner* — Danny Worrell
(74) *Attorney, Agent, or Firm* — Muncy, Geissler, Olds & Lowe, P.C.

(57) ABSTRACT

A method for making items of clothing having shape memory, the method comprising: synthesizing (31) a shape memory polyurethane; subjecting (34) the shape memory polyurethane to wet spinning, dry spinning, melt spinning or multi-component spinning in order to produce shape memory fibers; and knitting or weaving (36) the shape memory fibers to form the item of clothing.

8 Claims, 4 Drawing Sheets

(51) Int. Cl.
*A61F 13/08* (2006.01)
*D01F 6/70* (2006.01)

(56) References Cited

U.S. PATENT DOCUMENTS

| | | | |
|---|---|---|---|
| 4,990,545 A * | 2/1991 | Hourai et al. | 521/171 |
| 5,098,776 A * | 3/1992 | Kobayashi et al. | 442/104 |
| 5,128,197 A * | 7/1992 | Kobayashi et al. | 442/214 |
| 5,145,935 A * | 9/1992 | Hayashi | 528/65 |
| 6,281,262 B1 | 8/2001 | Shikinami | |
| 6,770,356 B2 * | 8/2004 | O'Donnell et al. | 428/297.4 |
| 6,933,421 B2 * | 8/2005 | Topolkaraev et al. | 604/361 |
| 7,309,104 B2 * | 12/2007 | Browne et al. | 297/284.1 |
| 8,163,376 B2 * | 4/2012 | Hayashi et al. | 428/292.1 |
| 2002/0115977 A1* | 8/2002 | Topolkaraev et al. | 604/385.24 |
| 2007/0156248 A1 | 7/2007 | Marco et al. | |
| 2010/0234779 A1* | 9/2010 | Asvadi et al. | 601/84 |
| 2012/0225600 A1* | 9/2012 | Rule et al. | 442/328 |

FOREIGN PATENT DOCUMENTS

| | | |
|---|---|---|
| WO | WO 03/088818 | 10/2003 |
| WO | WO 2006/071520 | 7/2006 |
| WO | WO 2006/092789 | 9/2006 |
| WO | WO 2008/148138 | 12/2008 |

OTHER PUBLICATIONS

Small.IV, W., Wilson, T.S., Benett, W.J., Loge, J.M. & Maitland, D.J., Laser-activated Shape Memory Polymer Intravascular Thrombectomy Device. Optics Express, 2005. 13: 8204-8213.

Small.IV, W., Metzger, M.F., Wilson, T.S. & Maitland, D.J., Laser-activated Shape Memory Memory Polymer Microactuator for Thombus Removal Following Ischemic Stroke: Preliminary in Vitro Analysis. IEEE Journal of Selected Topics in Quantum Electronics, 2005. 11: 892-901.

Buckley, P.R., McKinley, G.H., Wilson, T.S., IV, W.S., Bennett, W.J., Bearinger, J.P., McElfresh, M.W. & Maitland, D.J., Inductively Heated Shape Memory Polymer for the Magnetic Acuation of Medical Devices. IEEE Transactions on Biomedical Engineering, 2006. 53: 2075.

Schmidt, A.M., Electromagnetic Activation of Shape Memory Polymer Networks Containing Magnetic Nanoparticles. Macromolecular Rapid Communications, 2006. 27: 1168-1172.

Hampikian, J.M., Heaton, B.C., Tong, F.C., Zhang, Z. & Wong, C.P., Mechanical and Radiographic Properties of a Shape Memory Polymer Composite for Intracranial Aneurysm Coils. Materials Science and Engineering C, 2006. 26: 1373-1379.

Smart Surgery. Future Materials (through Textile Technology Index), 2004(1): 33-34.

Lendlein, A. & Langer, R., Biodegradable, Elastic Shape-Memory Polymers for Potential Biomedical Applications. Science, 2002. 96: 1673-1676.

Huang, W.M., Lee, C.W. & Teo, H.P., Thermomechanical Behavior of a Polyurethane Shape Memory Polymer Foam. Journal of Intelligent Material Systems and Structures, 2006. 17: 753-760.

Wache, H.M., Tartakowska, D.J., Hentrich, A. & Wagner, M.H., Development of a Polymer Stent with Shape Memory Effect as a Drug Delivery System. Journal of Materials Science: Materials in Medicine, 2004. 14: 109-112.

Liu, C., Mather, P.T. & Burstone, C. Proceedings of the Annual Technical Conference—Society of Plastics Engineers, 64th, Society of Plastics Engineers, Brookfield, CT, USA, pp. 1356-1360. 2006.

Lee, S. & Starner, T. Stop Burdening Your Eyes: a Wearable Electro-Tactile Display. 12th IEEE International Symposium on Wearable Computers, Pittsburgh, PA, USA. 2008.

Studstill, K., Emotion Sensing Dress Releases Mood Driven Scents, http://www.psfk.com/2010/01/emotion-sensing-dress-releases-mood-driven-scents.html. 2010.

Qi, K., Chen, X. & Liu, Y., Facile Preparation of Anatase/SiO2 Spherical Nanocomposites and Their Application in Self-cleaning Textiles. Journal of Materials Chemistry, 2007. 17: 3504-3508.

Lendlein, A. & Kelch, S., Shape-Memory Polymers. Angewandte Chemie International Edition, 2002. 41: 2034-2057.

Kim, B.K., Lee, S.Y. & Xu, M., Polyurethane Having Shape Memory Effect. Polymer, 1996. 37: 5781-5793.

Crowson, A. Smart Structures and Materials 1996: Smart Materials Technologies and Biomimetics. 1996. Smart Structures and Materials 1996: Smart Materials Technologies and Biomimetics: Proc. SPIE vol. 2716.

Tobushi, H., Hashimoto, T., N.Ito, Hayashi, S. & Yamada, E., Shape Fixity and Shape Recovery in a Film of Shape Memory Polymer of Polyurethane Series. Journal of Intelligent Material Systems and Structure, 1998. 9: 127-136.

Volk, B.L., Lagoudas, D.C. & Chen, Y.C. Thermomechanical Characterization of the Nonlinear, Rate Dependent Response of Shape Memory Polymers. in Proceedings of SPIE—The International Society for Optical Engineering, v 6929, Behavior and Mechanics of Multifunctional and Composite Materials 2008, p. 69291B, San Diego, CA, United States. 2008.

Maitland, D.J., Metzger, M.F., Schumann, D., Lee, A. & Wilson, T.S., Photothermal Properties of Shape Memory Polymer Micro-actuators for Treating Stroke. Lasers in Surgery and Medicine, 2002. 30: 1-11.

* cited by examiner

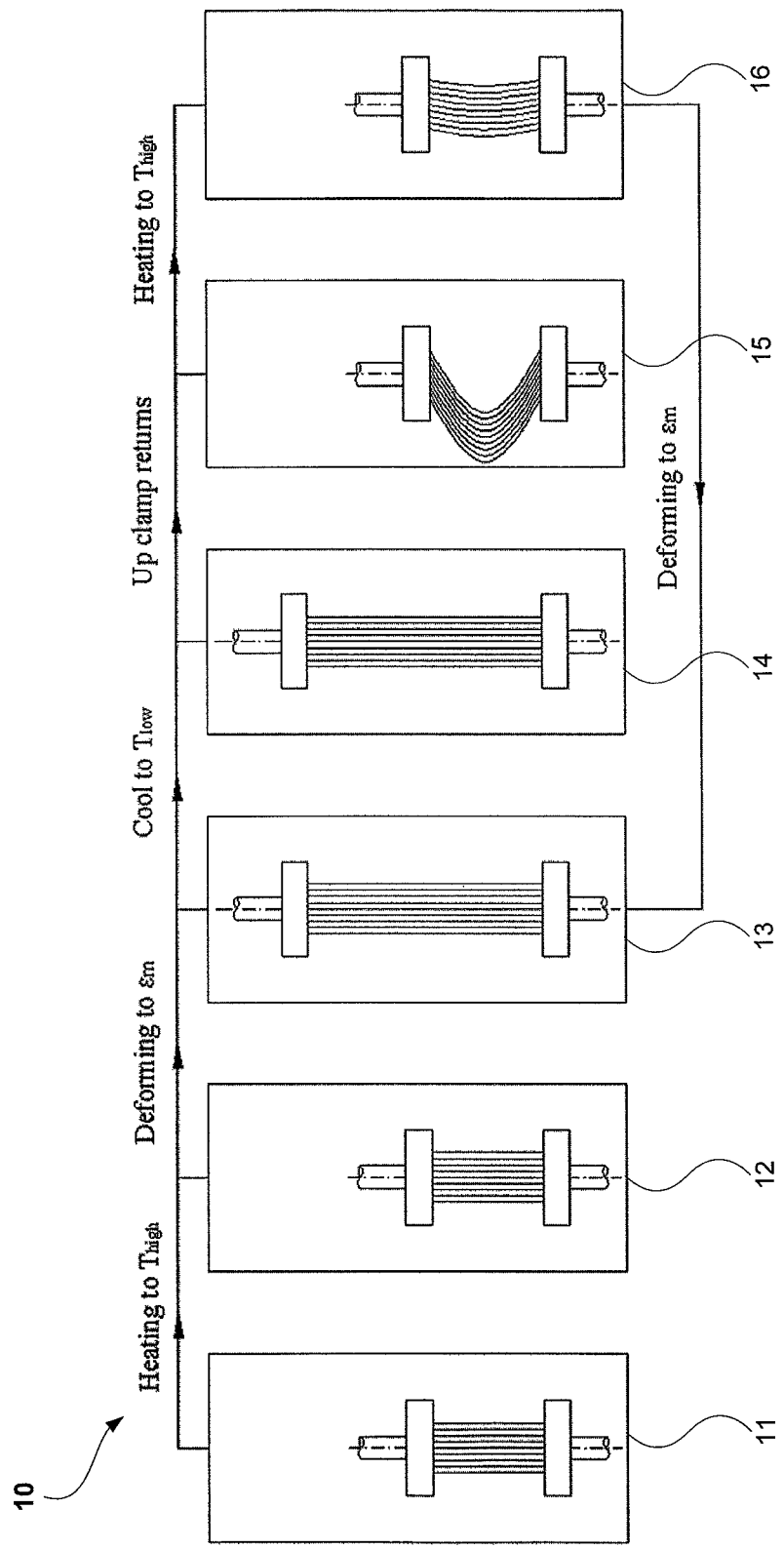

ITEMS OF CLOTHING HAVING SHAPE MEMORY

TECHNICAL FIELD

The invention concerns items of clothing having shape memory and a method for making items of clothing having shape memory.

BACKGROUND OF THE INVENTION

The profiles of human bodies are versatile and it is difficult to select a suitable undergarment or accessory for each individual. Sometimes, non-fitting garments or accessories may cause discomfort and even allergy to the individual due to inappropriate pressure exerted on their body. This problem becomes worse if the wearer participates in intense exercise. For example, conventional socks are usually made of elastic fibers or other synthetic fibers or a blend of the both. The sock top is normally made of elastic fibers or threads to increase the elasticity so that the sock does not easily to slide down the leg. However, the increased pressure exerted by the elastic fibers/threads on the leg is very uncomfortable. Secondly, the high-pressure may cause indentation marks on the skin of the leg after prolonged wearing. It has been found that the indentation by the socks can block blood circulation and therefore has a potential to be very harmful. Another example is waistbands that are normally made of elastic strips. After eating or after long distance traveling, the wearer will feel discomfort because the tightness of the waistbands increases significantly after the eating or prolonged travelling.

Pressure garments have been used to cure wounds and treat vascular problems. Pressure garments for healing wounds can reduce the effect of scaring whereas pressure garments for varicose veins are more effective in treating venous disorders than when no compression is applied. However, these pressure garments are made of conventional textiles and have problems during use. Firstly, a pressure garment especially a high-pressure cure garment type is so tight that they are difficult to wear. Secondly, traditional pressure garments have the tendency of loosening after wearing several times.

Shapes of garments and accessories made of traditional fabric after the garments and accessories are made cannot be changed into other shapes or styles. Although garments made from spandex fibers can be deformed to any shapes, the deformed shape cannot be fixed for aesthetic design because the spandex fibers shrink to the original length immediately when the external force is released.

Shape memory metallic alloy wires can be used in woven fabric for aesthetic design. The garments and accessories made of shape memory metallic alloys can change their shapes with varying environmental and human body temperature. However, there are many problems associated with the intrinsic properties of metallic alloy. Firstly, due to the significant differences of mechanical and surface properties of shape memory metallic alloy wires and traditional fabrics, shape memory metallic alloy wires have a tendency to protrude out of the fabric. Complicated structures of fabric with shape memory metallic alloy wires are difficult to accomplish. Secondly, due to the low extensibility and high stiffness of shape memory metallic alloy wires, knitting of shape memory metallic alloy wires is not easy to perform. If the structure of shape memory fabric with shape memory metallic alloy wires is not designed properly it will significantly affect the soft handling of the fabric.

Smart functional textiles are developing rapidly. Textiles with novel functions such as luminescent textiles, textiles display, emotion sensing dress, and self-cleaning textiles have been developed. However, significant developments in smart garments and accessories with shape memory functions are few.

SUMMARY OF THE INVENTION

In a first preferred aspect, there is provided an item of clothing having shape memory, comprising:
shape memory fibers made from shape memory polyurethane;

The shape memory polyurethanes may be a $T_m$ type shape memory polyurethane or a $T_g$ type shape memory polyurethane.

The item of clothing may further comprise yarns of ordinary natural or synthetic fibers.

The item of clothing may be a low-pressure undergarment or accessory from any one from the group consisting of: intimate apparel, socks, waistbands, stocking, hosiery, pants, and legging.

The shape memory fibers may have a thermal transition temperature from about 5° C. to 30° C.

The shape memory fibers may have a shape fixity ratio from about 10% to 50%, and a shape recovery ratio from about 90% to 100% measured by thermal drawing and thermal recovery.

The shape memory fibers may have a breaking elongation ratio from about 50% to 600%.

The shape memory fibers may have a recovery ratio of at least 50% measured by cold drawing and cold recovery.

The shape memory fibers may be subjected to drawing before knitting or weaving to produce a high-pressure garment, and the drawing is performed with a drawing temperature from about 22° C. to 50° C., and a drawing ratio from about 0.5 to 5.0.

The high-pressure garment or accessory may have a larger size than a body part of the wearer to be clothed by the item of clothing.

The shape memory fibers may have a thermal transition temperature from about 20° C. to 60° C.

The shape memory fibers may have a shape fixity ratio from about 30% to 100%, and a shape recovery ratio from about 75% to 100%, measured by thermal drawing and thermal recovery.

The shape memory fibers may have a breaking elongation ratio from about 20% to 500%.

The high-pressure garment may be any one from the group consisting of: pressure socks, stocking, and legging.

The shape memory fibers may be woven or knitted spaciously and loosely according to a predetermined value such that there is sufficient space for a shape memory effect to occur to produce an item of clothing with a dynamic aesthetic design.

The dynamic aesthetic design may be dynamic creasing recovery or style changing.

For dynamic creasing recovery, the shape memory fibers may have a shape recovery ratio of at least 90% and a shape fixity ratio of at least 95%.

For dynamic creasing recovery, the shape memory fibers may have a thermal transition temperature from about 20° C. to 65° C.

For style changing, the shape memory fibers may be subjected to drawing before knitting or weaving, and the drawing temperature is from about 20° C. to 150° C. with a drawing ratio from about 0.5 to 5.0.

For style changing, the shape memory fibers may have a shape recovery ratio from about 70 to 100%; and a shape fixity ratio from about 70% to 100%.

For style changing, the shape memory fibers may have a thermal transition temperature from about 20° C. to 65° C.

The shape memory polyurethane may be synthesized by solution polymerization or bulk polymerization.

The shape memory polyurethane may be subjected to wet spinning, dry spinning, melt spinning or multi-component spinning in order to produce shape memory fibers.

In a second aspect, there is provided a method for making items of clothing having shape memory, the method comprising:
synthesizing a shape memory polyurethane;
subjecting the shape memory polyurethane to wet spinning, dry spinning, melt spinning or multi-component spinning in order to produce shape memory fibers; and
knitting or weaving the shape memory fibers to form the item of clothing.

The shape memory polyurethane may be synthesized by solution polymerization or bulk polymerization.

The method may further comprise drawing the shape memory fibers before knitting or weaving the shape memory fibers to produce a high-pressure garment, and the drawing is performed with a drawing temperature from about 22° C. to 150° C., and a drawing ratio from about 0.5 to 5.0.

The shape memory fibers may be knitted or woven spaciously and loosely according to a predetermined value such that there is sufficient space for a shape memory effect to occur to produce an item of clothing with a dynamic aesthetic design The method may further comprise drawing the shape memory fibers before knitting or weaving, and the drawing temperature is from about 20° C. to 150° C. with a drawing ratio from about 0.5 to 5.0, to produce a an item of clothing with a style changing dynamic aesthetic design.

Shape memory polymers differ from conventional polymers because they have a physically crosslinked or chemically crosslinked structure to support the shape memory polymers at a high temperature, and a thermal transition temperature at a low temperature such as around or above ambient temperature acting as a shape switch. After deforming shape memory polymers, they are able to restore to their original shape upon heating above the thermal transition temperature. The shape switch can either be a glass transition ($T_g$) or a melting transition ($T_m$) temperature. According to thermal transition types used as the thermal transition temperature, shape memory polymers fall into $T_m$ type shape memory polymers and $T_g$ type shape memory polymers.

Shape memory fibers can sense the environmental temperature and respond to the temperature variation by shape variation. This enables the creation of intelligent garments and accessories with self-regulating structures and performance in response to environmental and human body temperature.

Therefore shape memory fibers may be used in different kinds of garments and accessories to enable smart wearing functionality. The shape memory garments and accessories with smart wearing functionality include: low-pressure shape memory undergarments and accessories, high-pressure shape memory garments and accessories, and shape memory garments and accessories with dynamic aesthetic design.

The preparation of the corresponding shape memory fibers used in smart textile products is also provided by the present invention.

BRIEF DESCRIPTION OF THE DRAWINGS

An example of the invention will now be described with reference to the accompanying drawings, in which:

FIG. 1 is a process flow diagram of a thermomechanical cyclic tensile testing process of shape memory fibers by thermal drawing and thermal recovery in accordance with an embodiment of the present invention;

DETAILED DESCRIPTION OF THE DRAWINGS

Figure 2A:
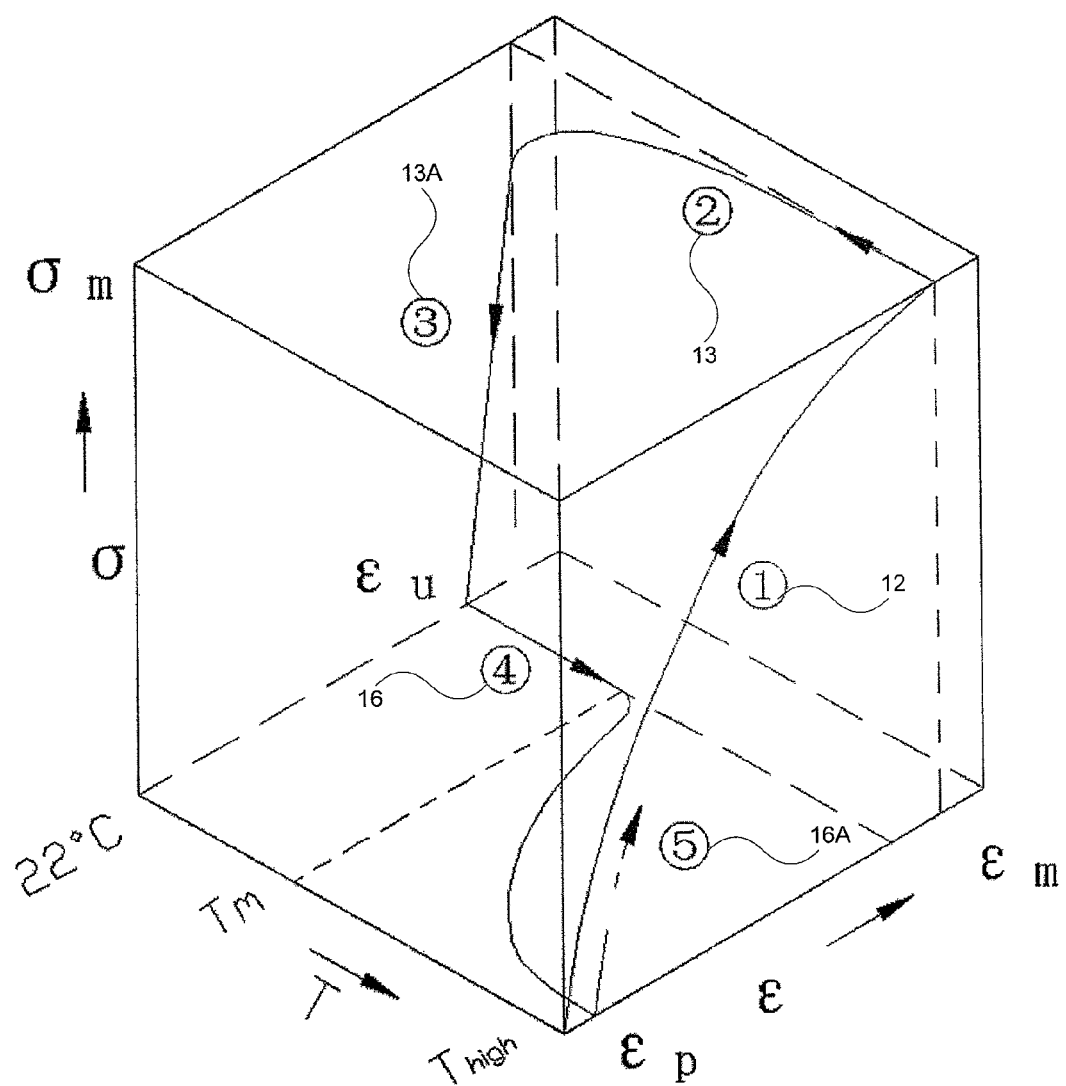
FIG. 2(a) is a chart depicting cyclic tensile testing path under thermal drawing thermal recovery.

Referring to the drawings, the shape memory fibers are made of shape memory polymers. The shape memory fibers are used to prepare garments and accessories for the following purposes: low-pressure shape memory undergarments and accessories, high-pressure shape memory garments and accessories, shape memory garments and accessories with dynamic aesthetic design.

Low-pressure Shape Memory Undergarments and Accessories

The garments and accessories made of shape memory fibers can improve the comfort sensation of textile products such as intimate apparel. This can be attributed to the fixity of shape memory fibers to temporary shapes, which diminishes most of the pressure sensation to wearers. The undergarments and accessories made of shape memory fibers with a human body thermal transition temperature become soft and flexible to adapt to the profile of the wearer. For example, the socks tops made of shape memory fibers can give a comfort sensation no indentation marks are produced on the skin of the leg. The waistbands made of shape memory fibers and yarns can adjust their length according to the variation of the waist of the wearer. The low-pressure garments and accessories made of shape memory fibers will not have any influence on the blood circulation of the human body as those products made of elastic fibers or threads.

The fabrics made of shape memory fibers have relative low vertical tension exerting on the skin compared to fabrics made of elastic fibers (spandex fibers) and other fibers in vertical pressure tests. In contrast, the garments and accessories made of elastic fibers (threads) exert significant pressure on the wearer because elastic fibers do not have shape fixity. The fabrics made of shape memory fibers can therefore improve the comfort sensation of textile products especially for undergarments and accessories such as intimate apparel, socks, waistbands, stocking, hosiery, pants, and legging, which are in close contact with the skin of the wearer.

The switch temperature of shape memory fibers for low-pressure garments and accessories is in the range of 5 to 30° C. and the breaking elongation is in the range of 50 to 600%. The shape fixity of the shape memory fibers is in the range of 10 to 50%, and the shape recovery above 90% tested by thermal drawing and thermal recovery. The shape memory fibers for low-pressure shape memory undergarments and accessories also have a certain degree of elasticity with a recovery ratio of above 20% by cold drawing and cold recovery. Therefore the low-pressure undergarments and accessories can fit well to the profile of human bodies. The low-pressure shape memory undergarment and accessories with comfort sensation are made solely from shape memory fibers or in blends of the shape memory fibers with natural or synthetic fibers.

High-pressure Shape Memory Garments and Accessories

Shape memory fibers for high-pressure garments and accessories are subjected to drawing before knitting or weaving. The drawing temperature is in the range of 20 to 150° C. with a drawing ratio 0.5 to 5.0. The high-pressure garments and accessories made of the shape memory fibers, after being heated, can shrink to a shape with a very small size which is referred to as a stabilized shape. By heating, the high-pressure garments and accessories can be softened and enlarged into a larger size than that of the wearer's body or body part of the wearer. The enlarged shape can be temporarily fixed by cooling the garments and accessories to a low temperature. Therefore, the high-pressure garments and accessories are easy to wear. Then, by heating, the pressure garments and accessories have a tendency to shrink and recover to their stabilized shape. Therefore, the pressure garments and accessories can fit well for the wearer and exert suitable pressure on the skin. The high-pressure garments and accessories can also be easily removed from the wearer by heating them using a hair drier or hot water after they become soft again. The high-pressure shape memory garments and accessories can be repeatedly used.

The pressure garments and accessories are fabricated by knitting or weaving shape memory fibers alone or yarns of the shape memory fibers with yarns of ordinary natural or synthetic fibers. The pre-drawing and structure of the garment determines the original initial size of the garment after knitting. A minimal size of the garment can be obtained by heating the garment in hot water or by using a hair dry by free shrinkage. The size of the wearer's body part should be in the range from about the original initial size to the minimal size. Through proper shape memory, pre-drawing and garment structure design, selectively adjustable pressure can be exerted on the skin of the wearer.

The thermal transition temperature of the shape memory fiber for high-pressure shape memory garments and accessories is in the range of 20 to 60° C. The shape memory fiber has a shape fixity ratio in the range of 30 to 100%, the shape recovery ratio in the range of 75 to 100%, tested by thermal drawing and thermal recovery. The breaking elongation ratio of the shape memory fiber should be in the range of 20 to 500%. The high-pressure garments or accessories include pressure socks, stocking, legging, and other pressure garments but not limited to these.

Shape Memory Garments and Accessories with Dynamic Aesthetic Design

Shape memory fibers, yarns and fabrics can be used for aesthetic design. In comparison with shape memory metallic alloy wires for dynamic aesthetic design, shape memory polymeric fibers can give the look and feeling similar to conventional clothing fabrics; and have better compatibility with human bodies. Furthermore, shape memory fibers are much cheaper compared to shape memory metallic alloy wires. Shape memory fabrics have better capabilities for 3D textiles than spandex and polyester fiber due to their good shape fixity.

For example, in shape memory fabrics, the shape memory fibers can be woven or knitted spaciously and loosely so as to provide enough room for the shape memory effect to occur. Contraction (shape recovery) occurs when the environmental temperature increases. Therefore, fabrics with shape memory fibers can show dynamic aesthetic design due to varying temperature. A number of aesthetic design features can be achieved by using shape memory fabrics.

For shape memory garments and accessories with dynamic aesthetic design, different kinds of shape memory fibers are used depending on the desired effect. The dynamic aesthetic design may be dynamic creasing recovery or style changing but not limited to these. For dynamic creasing recovery garments and accessories, the shape memory fixity of the shape memory fibers should be above 95% and shape recovery above 90% tested by thermal drawing and thermal recovery. For style changing garments and accessories, the shape memory fibers have to be subjected to pre-drawing on rollers before weaving or knitting. The pre-draw ratio is in the range of 0.5 to 5.0. The treatment temperature of the process is in the range of 20 to 150° C. The shape recovery ratio of the shape memory fibers obtained is in the range of 70 to 100%; and shape fixity in the range of 70 to 100% tested by thermal drawing and thermal recovery. The thermal transition temperature of the shape memory fibers for dynamic aesthetic design is in the range of 20 to 65° C.

The shape memory fibers for achieving the functions described are made of shape memory polyurethanes. The shape memory polyurethanes are synthesized from three starting materials: long chain polyol, diisocyanate, and chain extender. Diisocyanate and chain extender form the hard segment and the long chain polyol forms the soft segment.

Depending on the desired properties on the shape memory garments and accessories, the shape memory polyurethanes used to fabricate shape memory fibers are two types: $T_m$ type shape memory polyurethane and $T_g$ type shape memory polyurethane. The polyols for $T_g$ type shape memory polyurethanes are tabulated in Table 1. The polyols for $T_m$ type shape memory polyurethanes are tabulated in Table 2. The diisocyanate for the shape memory polyurethanes are shown in Table 3. The molecular extenders for the shape memory polyurethanes are presented in Table 4. Alternatively, the chemicals may be a mixture of polyols, co-polyols, mixed diisocyanate, modified diisocyanate or mixed molecular extenders.

TABLE 1

Polyols for $T_g$ type shape memory polyurethane

| Polyol | Molecular weight (Mn) |
|---|---|
| Polypropylene glycol (Mn:) | 250~650 |
| Polytetramethylene glycol | 250~650 |
| Polyethylene glycol | 250~650 |
| Poly (1,6-hexylene adipate) diol | 250~650 |
| Poly (1,4-butylene adipate) diol | 250~650 |
| Poly (ethylene adipate) diol | 250~650 |
| Poly (1,2-propylene adipate) diol | 250~650 |
| Polycaprolactone diol | 250~650 |
| Polycarbonate diol | 250~650 |
| Bisphenol A + propylene oxide | 300~800 |
| Bisphenol A + ethylene oxide | 300~800 |

TABLE 2

Polyols for $T_m$ type shape memory polyurethanes

| Polyol | Molecular weight (Mn) |
|---|---|
| Poly (1,6-hexylene adipate)diol | Mn: >3000 |
| Poly (1,4-butylene adipate)diol | Mn: >3500 |
| Polycaprolactone diol | Mn: >3500 |

TABLE 3

Diisocyanate for shape memory polyurethanes

| Diisocyanate | Molecular weight (Mn) |
|---|---|
| isophorone diisocyanate | 222 |
| methylene-bis(4-cyclohexylisocyanate) | 262 |

TABLE 3-continued

Diisocyanate for shape memory polyurethanes

| Diisocyanate | Molecular weight (Mn) |
| --- | --- |
| 1,6-hexamethylene diisocyanate | 168 |
| 4,4'-diphenylemethane diisocyanate | 250 |
| 2,4-tolulene diisocyanate | 174 |
| tetramethylxylene diisocyanate | 244 |
| 1,4-Phenylene diisocyanate | 160 |

TABLE 4

Molecular extenders for shape memory polyurethanes

| Molecular extenders | Molecular weight (Mn) |
| --- | --- |
| 1,3-propanediol | 76 |
| 1,4-butanediol | 90 |
| 1,2-ethanediol | 62 |
| 1,6-Hexanediol | 118 |
| 4,4'-dihydroxy biphenyl | 186 |
| 2,2-bis(hydroxymethyl)propionic acid | 134 |
| hydroquinone bis(2-hydroxyethyl)ether | 198 |
| 4,4'-bis(2-hydroxyethoxy)biphenyl | 274 |
| 4,4'-bis(6-hydroxyhexoxy)biphenyl | 414 |
| Bis(p-hydroxymethylphenyl)terephthalate | 378 |
| 4,4'-(1,4-phenylene bis(methylldynenltrilo))diphenylethanol | 372 |
| bisphenol A | 228 |
| N-bis(2-hydroxyethyl)-isonicotinamide | 210 |
| N-methyldiethanolamine | 119 |
| bisphenol A ethoxylate | 404 |
| 1,2-diaminoethane | 60 |
| 1,2-diaminopropane | 74 |
| polyhedral oligomeric silsesquioxanes | 1017 |
| N,N-dis(2-hydroxyethyl)-isonicotinamide | 210 |
| N-methyldiethanolamine | 119 |

Figure 3:
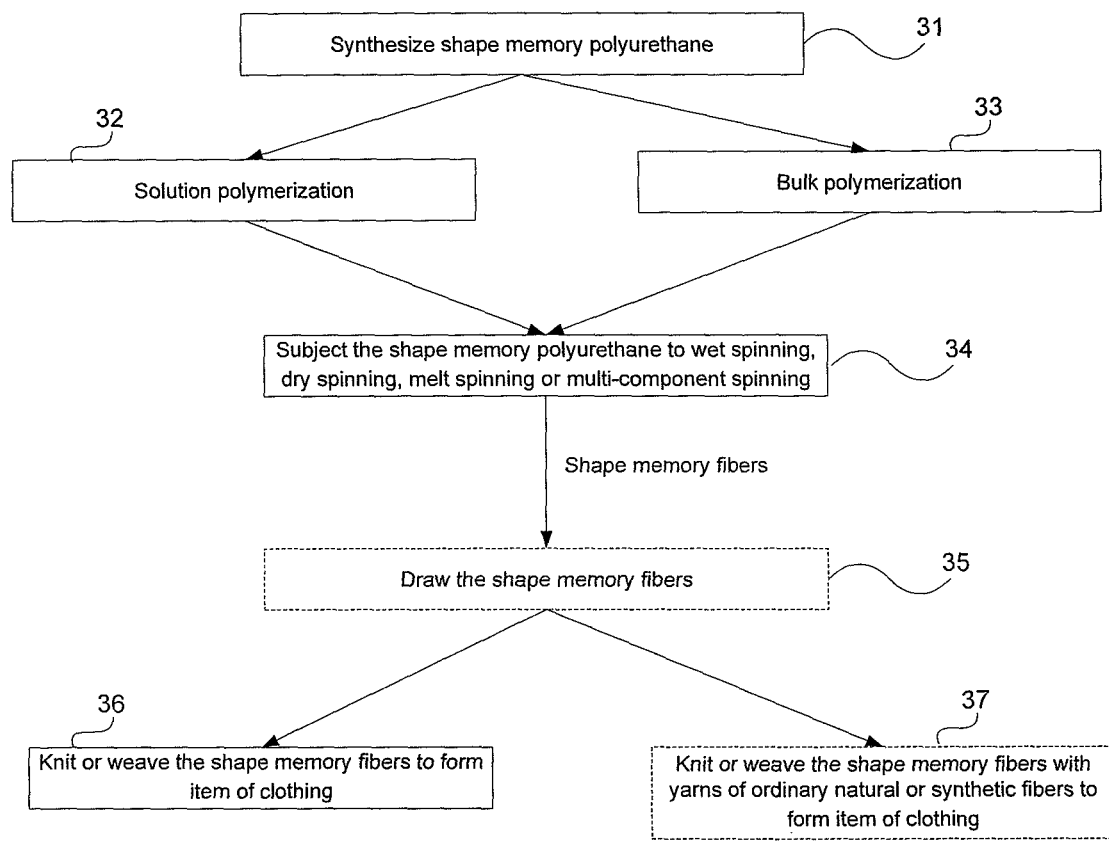
FIG. 3 is a process flow diagram of a method for making items of clothing having shape memory in accordance with an embodiment of the present invention.

Referring to FIG. 3, the shape memory polyurethane can be synthesized (31) by bulk polymerization (33) or solution polymerization (32). In bulk polymerization process, a one-step polymerization or a two-step polymer method can be used. In a one-step polymerization process, all the chemicals are added to the reactor at the same time. In a two-step polymerization process, the polyol is first end caped with isocyanate moieties at both ends; and then extended with small sized diols or diamines. In solution polymerization, solvent is used during the synthesis. Suitable solvents can be selected from the group consisting of N,N-dimethylformamide, Dimethylformamide, N,N-dimethylacetamide, 1-methyl-2-pyrrolidinane, methyl sulfoxide or mixture thereof.

The shape memory polyurethanes are then processed to produce shape memory fibers. Spinning techniques (34) are used to process the shape memory polyurethanes including: wet, dry, and melt spinning.

In wet spinning, the solid concentration of shape memory polyurethane is adjusted to 20 to 40 wt % and viscosity of 5 to about 200 Pa·S. The spinning solution is heated and maintained at a certain temperature if necessary. The shape memory fiber is extruded out from a spinneret and precipitated in a coagulation bath. Then, the shape memory fiber is subjected to heat treatment and postdrawing (35), if necessary.

In dry spinning, the solid concentration of shape memory polyurethane is in the range of 25 to 40 wt %. The polymer solution is extruded through a fiber spinneret. After the fiber is pumped out of the spinneret, hot air is used to evaporate the solvent.

In melt spinning, the shape memory polymer is melted and extruded though a fiber spinneret and solidified by cooling.

The shape memory fibers may also be prepared via multi-component spinning for more special properties. In multi-component spinning, two or more polymer melts may be used, at least one of which is a shape memory polyurethane. The shape memory fibers prepared can be in the form of cylindrical fibers, hollow fibers, or any abnormal fibers.

Finally, the shape memory fibers alone are knitted or weaved (36) to form the garment or clothing item. Alternatively, the shape memory fibers and yarns of ordinary natural or synthetic fibers are knitted or weaved (37) to form the garment or clothing item.

Testing

The shape recovery properties of the shape memory fibers are evaluated by thermomechanical cyclic tensile testing by thermal drawing and thermal recovery. The thermomechanical cyclic tensile testing was carried out using a tensile tester Instron 4466 (Instron Corporation of USA) equipped with a temperature controllable chamber. The elastic recovery properties of the shape memory fibers were evaluated by cold drawing and cold recovery.

Turning to FIG. 1, the programmed thermomechanical cyclic tensile testing process by thermal drawing and thermal recovery is shown.

The sample is heated (11) to temperature $T_{high}$ ($T_{high}$=thermal transition temperature+15° C.). Then, the heated sample is stretched (12) to 100% elongation ratio at the at a drawing speed of 10 mm/min. Cool air is vented (13) passively into the chamber to cool down the sample to 22° C. and the temperature is maintained at this temperature for 15 minutes to fix (13A) the temporary elongation. The upper clamp is returned (14) to the original position at a speed of 40 mm/min and the sample shrank (15) from 100% to $\epsilon_u$ because of instant elastic recovery. $\epsilon_u$ is the strain after unloading at $T_{low}$. Finally, the sample is heated (16) to $T_{high}$ to allow the shape memory recovery with result sample elongation returned to $\epsilon_p$. $\epsilon_p(N)$ is the residual strain after recovering in the $N^{th}$ cycle. After the cycle is completed, a second cycle begins (16A). The cyclic tensile testing path is shown in FIG. 2(a).

Figure 2B:
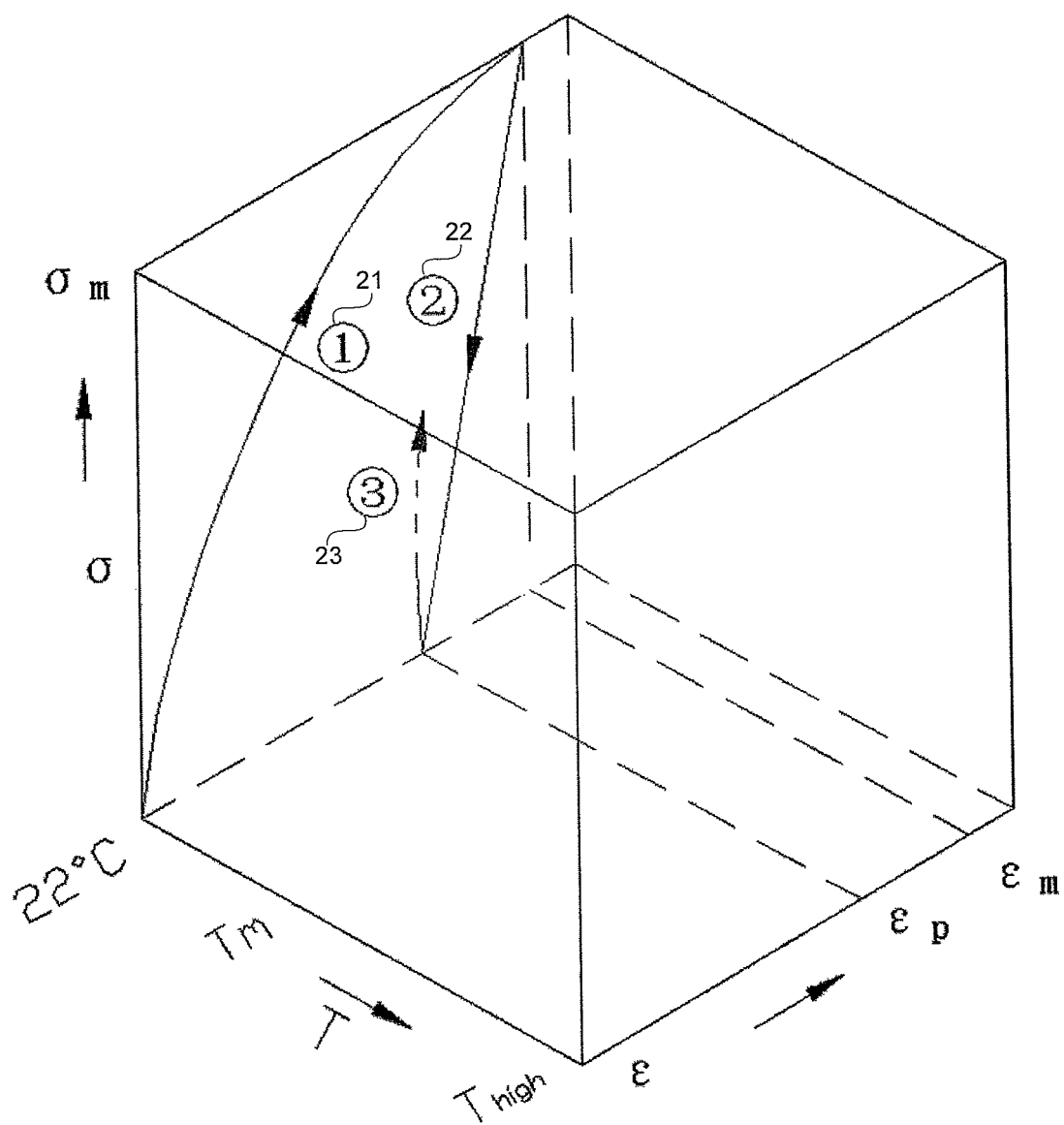
FIG. 2(b) is a chart depicting cyclic tensile testing path under cold drawing and cold recovery.

Referring to FIG. 2(b), the cold drawing (ambient temperature) and cold recovery cyclic tensile testing is shown. The fibers were stretched (21) to 100% strain at a speed of 10 mm min$^{-1}$ at ambient temperature and kept at 100% strain the temperature for 15 mins. The clamps were unloaded (22) and allowed to return to their original position. The above cycle was repeated (23).

The above cycle may be repeated several times and the stress-strain was recorded for analysis. In FIGS. 2(a) and 2(b), $\epsilon_m$ is the maximum strain in the cyclic tensile tests. $\sigma_m$ is the maximum stress at the maximum strain $\epsilon_m$. $\epsilon_u$ is the strain after unloading at $T_{low}$, and $\epsilon_p(N)$ is the residual strain after recovering in the $N^{th}$ cycle. The $\epsilon_m$ value is set at 100% strain for the study. The fixity ratio ($R_f(N)$) and recovery ratio ($R_r(N)$) at the $N^{th}$ cycle and total recovery ratio ($R_{r\text{-}tot}$) after the $N^{th}$ cycle are calculated by the following equations:

$$R_f(N)=\epsilon_u(N)$$

$$R_r(N)=(1-\epsilon_p(N))/(1-\epsilon_p(N-1))\times 100\%$$

$$R_{r\text{-}tot}=(1-\epsilon_p(N))\times 100$$

EXAMPLES

A first example of a pressure cure garment is described. A $T_m$ type shape memory polyurethane was synthesized by using poly(1,6-hexylene adipate)diol-3000 as the soft segment, 4,4'-diphenylemethane diisocyanate and 1,4-butanediol as the hard segment. The polyurethane was prepared by the one-step polymerization method. The shape memory fiber was prepared from the polyurethane by melt spinning. The shape memory fiber was subjected to post-drawing at a temperature 22° C. with a draw ratio 4.0. The thermal transition temperature of the prepared shape memory fiber was a melting temperature at 40° C. The shape memory fiber had a tenacity of 3.0 cN/dtex, and breaking elongation 50%. The shape recovery ratio and fixity ratio of the shape memory fiber were 100% and 85% respectively tested by thermal drawing and thermal recovery.

A cuff was knitted from prefixed shape memory fibers and nylon yarns. The width of grey cloth is 14 cm and after the heating slacking the width is 7 cm. The cuff is hard to stretch under normal temperature but it became softer after heating above switch temperature and easy to wear. The pressure of the cuff is enough for pressure cure and can sustain the higher-pressure level.

A second example of a shape memory hosiery is described. A $T_g$ type shape memory polyurethane was synthesized by using polytetramethylene glycol-650 as the soft segment, while 4,4-diphenylmethane diisocyanate, and 1,4-butanediol as the hard segment by bulk polymerization. The polyurethane was prepared by the two-step method. Pre-polymers were first prepared by terminating polytetramethylene glycol with 4,4-diphenylmethane diisocyanate at both ends. Then the molecules were extended with 1,4-butanediol. The shape memory fiber was subjected to pre-drawing at temperature 20° C. with a draw ratio 2.0. The prepared shape memory fiber had a tenacity of 2.5 cN/dtex, and breaking elongation 50%. The shape fixity ratio of the shape memory fiber was 70% and recovery ratio of 80% respectively tested by thermal drawing and thermal recovery. The thermal transition temperature of the shape memory fiber was a glass transition temperature at 55° C.

Hosiery was knitted from shape memory fibers and polyester fibers on a seamless machine. The hosiery can be easily stretched and put on after being heated above the thermal transition temperature.

A third example of a pressure stocking is described. A $T_g$ type shape memory polyurethane was synthesized by using polytetramethylene glycol-650 as the soft segment, while 4,4-diphenylmethane diisocyanate, and 1,4-butanediol as the hard segment by bulk polymerization. The polyurethane was prepared by the two-step method. Pre-polymers were first prepared by terminating polytetramethylene glycol with 4,4-diphenylmethane diisocyanate at both ends. Then the molecules were extended with small size 1,4-butanediol. The shape memory fiber was subjected to post-drawing at temperature 20° C. with a draw ratio 2.0. The prepared shape memory fiber had a tenacity of 2.5 cN/dtex and breaking elongation 50%. The shape fixity ratio of the shape memory fiber was 70%; and recovery ratio was 80% tested by thermal drawing and thermal recovery. The thermal transition temperature of the shape memory fiber was a glass transition temperature at 55° C.

A pressure stocking was knitted from the prefixed shape memory fibers and nylon yarns. The instep and sole used 250D shape memory fibers; the part from ankle to leg used 200D shape memory fibers; and the part from leg to thigh used 150D shape memory fibers. The structure of the whole stocking was one course 70D nylon plain jersey and one course 1+3 fake rib. The pressure gradient was formed. The stocking was easy to wear after heating and stretching. The stocking gave a higher pressure when being heated again.

A fourth example of a sock is described. A $T_g$ type shape memory polyurethane was synthesized by using polytetramethylene glycol-650 as the soft segment, while 4,4'-diphenylemethane diisocyanate and 1,4-butanediol as the hard segment. The polyurethane was prepared by the one-step polymerization method. The shape memory fiber was prepared from the polyurethane by melt spinning. The thermal transition temperature of the prepared shape memory fiber was a glass transition temperature at 20° C. The shape memory fiber had a tenacity of 1.1 cN/dtex, and breaking elongation 300%. The shape recovery ratio and fixity ratio of the shape memory fibers were 85% and 20% respectively which were tested by thermal drawing and thermal recovery.

A sock was knitted using the shape memory fibers of 150D and Nylon yarn in sock top and 20/15-shape memory fiber/Nylon cover yarn in other parts on a conventional machine of sock fabrication. After dyeing and heat setting, the sock had the same appearance as common socks and had comfortable elasticity. The sock had smaller pressure on ankle than that of a same sized sock made of spandex and other fiber.

A fifth example of a waistband is described. A $T_g$ type shape memory polyurethane was synthesized by using polytetramethylene glycol-650 as the soft segment, while 4,4'-diphenylemethane diisocyanate and 1,4-butanediol as the hard segment. The polyurethane was prepared by the one-step method bulk polymerization. The shape memory fiber was prepared from the polyurethane by melt spinning. The thermal transition temperature of the prepared shape memory fiber was a glass transition temperature at 25° C. The shape memory fiber had a tenacity of 1.2 cN/dtex, and breaking elongation 250%. The shape recovery ratio and fixity ratio of the shape memory fiber were 80% and 30% respectively which were tested by thermal drawing and thermal recovery.

The above shape memory fiber and 32S cotton yarn were used to knit a waistband of seamless pants. The waistband could fit the waistline when wearing. When the wearer sat down or was full from eating, the waistband would sense the body temperature and elongate to fit the larger waistline while did not cause a constricted feeling on the wearer's waist.

A sixth example of crease garments is described. A $T_g$ type shape memory polyurethane was prepared by the two-step methods. Polytetramethylene glycol-650 was used as the soft segment, while 4,4'-diphenylemethane diisocyanate and 1,4-butanediol were used as the hard segment. The polyols were first terminated with 4,4'-diphenylemethane diisocyanate at both ends to prepare pre-polymers.

Then the pre-polymers were extended with small size 1,4-butanediol. Shape memory fiber was fabricated from the shape memory polyurethane by melt spinning. The fiber was not subjected to post-drawing after spinning. The prepared shape memory fiber had a tenacity of 1.3 cN/dex and breaking elongation 150%. The thermal transition temperature of the shape memory fiber was a glass transition temperature at 60° C. The shape recovery ratio and fixity ratio of the shape memory fiber were both 90% tested by thermal drawing and thermal recovery.

A garment was made from cotton fabric and shape memory fabrics. The shape memory fabrics were woven or knitted using the shape memory fiber with high shape fixity. The garment gave exactly the same hand feeling as the cloth made of common natural or synthetic fibers. When the garment was creased by hand, it wrinkled and kept the appearance if it was not heated again. The garment could remember any creased shape and maintain the temporary designed crease.

A seventh example of a skirt is described. A $T_m$ type shape memory polyurethane was synthesized by using poly(1,6-hexylene adipate)diol-3000 as the soft segment, while 4,4'- diphenylemethane diisocyanate and 1,4-butanediol as the hard segment. The one-step polymerization method was employed to synthesize the shape memory polyurethane. The shape memory fiber was first prepared from the shape memory polyurethane by melt spinning. Then the shape memory fiber was subjected to post-drawing at 25° C. with a drawing ratio 4.0. The tenacity of the prepare shape memory fiber was 3.0 cN/dtex with a breaking elongation 50%. The thermal transition temperature of the shape memory fiber was a melting transition temperature at 40° C. The shape recovery ratio and fixity ratio of the shape memory fiber were 100% and 85% respectively tested by thermal drawing and thermal recovery.

A skirt was made from the above shape memory fibers which had high shape memory fixity and shape recovery force. The original length of the skirt was 60 cm. After heating the skirt above the thermal transition temperature, the skirt became shorter and changed into a mini skirt.

It will be appreciated by persons skilled in the art that numerous variations and/or modifications may be made to the invention as shown in the specific embodiments without departing from the scope or spirit of the invention as broadly described. The present embodiments are, therefore, to be considered in all respects illustrative and not restrictive.

We claim:

1. A method for making items of clothing having shape memory, the method comprising:
    synthesizing a shape memory polyurethane;
    subjecting the shape memory polyurethane to wet spinning, dry spinning, melt spinning or multi-component spinning in order to produce shape memory fibers;
    drawing the shape memory fibers with a drawing ratio of about 0.5 to 5.0; and
    after drawing the shape memory fibers, knitting or weaving the shape memory fibers to form the item of clothing.

2. The method according to claim 1, wherein the shape memory polyurethane is synthesized by solution polymerization or bulk polymerization.

3. A method for making items of clothing having shape memory, the method comprising:
    synthesizing a shape memory polyurethane;
    subjecting the shape memory polyurethane to wet spinning, dry spinning, melt spinning or multi-component spinning in order to produce shape memory fibers; and
    knitting or weaving the shape memory fibers to form the item of clothing; and
    further comprising drawing the shape memory fibers before knitting or weaving the shape memory fibers to produce a high-pressure garment, and the drawing is performed with a drawing temperature from about 22° C. to 50° C., and a drawing ratio from about 0.5 to 5.0.

4. The method according to claim 1, wherein the shape memory fibers are knitted or woven spaciously and loosely according to a predetermined value such that there is sufficient space for a shape memory effect to occur to produce an item of clothing with a dynamic aesthetic design.

5. The method according to claim 4, wherein the drawing temperature is from about 20° C. to 150° C.

6. A method for making items of clothing having shape memory, the method comprising:
    providing polyurethane shape memory fibers that have been drawn with a drawing ratio of about 0.5 to 5.0; and
    knitting or weaving the drawn shape memory fibers to form the item of clothing.

7. The method of claim 6, wherein providing polyurethane shape memory fibers that have been drawn comprises providing shape memory fibers and drawing the provided shape memory fibers with a drawing ratio of about 0.5 to 5.0.

8. The method of claim 7 including drawing the shape memory fibers at a drawing temperature of about 22° C. to 50° C.

\* \* \* \* \*